(12) United States Patent
Waddell

(10) Patent No.: US 10,128,075 B2
(45) Date of Patent: *Nov. 13, 2018

(54) ION GENERATION DEVICE HAVING ATTACHMENT DEVICES

(71) Applicant: Charles Houston Waddell, Roanoke, VA (US)

(72) Inventor: Charles Houston Waddell, Roanoke, VA (US)

(73) Assignee: Global Plasma Solutions, Inc., Savannah, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/297,547

(22) Filed: Oct. 19, 2016

(65) Prior Publication Data
US 2017/0133189 A1   May 11, 2017

Related U.S. Application Data

(60) Provisional application No. 62/243,175, filed on Oct. 19, 2015.

(51) Int. Cl.
*H01J 27/02* (2006.01)
*A61L 9/22* (2006.01)

(52) U.S. Cl.
CPC .............. *H01J 27/028* (2013.01); *A61L 9/22* (2013.01); *H01J 27/022* (2013.01)

(58) Field of Classification Search
CPC .......... H01J 27/00; H01J 27/02; H01J 27/028; H01J 27/022; H01J 37/08; H01J 37/16; H01T 23/00
See application file for complete search history.

(56) References Cited

U.S. PATENT DOCUMENTS

| | | | |
|---|---|---|---|
| 6,176,977 B1 * | 1/2001 | Taylor | B01D 53/32 123/539 |
| 8,795,590 B1 † | 8/2014 | Ellis | |
| 9,025,303 B2 * | 5/2015 | Waddell | H01T 23/00 361/231 |
| 2010/0175391 A1 * | 7/2010 | Jee | B60H 3/0071 62/3.1 |
| 2013/0336838 A1 * | 12/2013 | Waddell | A61L 2/14 422/4 |
| 2014/0078639 A1 * | 3/2014 | Waddell | H01T 23/00 361/230 |
| 2015/0157755 A1 † | 6/2015 | Ellis | |
| 2016/0190772 A1 † | 6/2016 | Sunshine | |

OTHER PUBLICATIONS

"Products" Web Page, http://rgfairpurification.com:80/products.html, 7 pages, Feb. 6, 2015, retrieved from Internet Archive Wayback Machine, https://web.archive.org/web/20150206005505/http://rgfairpurification.com:80/products.html#bipolar on Nov. 6, 2017.†

* cited by examiner
† cited by third party

*Primary Examiner* — Thai Pham
(74) *Attorney, Agent, or Firm* — Seth L. Hudson; Clements Bernard Walker, PLLC

(57) ABSTRACT

The present invention provides methods and systems for an ion generator device that includes a base, a generally circular sidewall projecting from the base forming an interior storage compartment and defining an upper edge, a top portion engaged to the upper edge, at least one high voltage wire extending from the device, and a power supply for providing a voltage to the high voltage wire for producing ions.

19 Claims, 8 Drawing Sheets

ION GENERATION DEVICE HAVING ATTACHMENT DEVICES

CROSS REFERENCE TO RELATED PATENT APPLICATION

The present patent application/patent claims the benefit of priority of co-pending U.S. Provisional Patent Application No. 62/243,175, filed on Oct. 19, 2015, and entitled "ION GENERATION DEVICE," the contents of which are incorporated in full by reference herein.

FIELD OF THE INVENTION

The present invention relates generally to the field of air treatment, and more particularly to the treatment of air using ionization.

BACKGROUND OF THE INVENTION

Air and other fluids are commonly treated and delivered for a variety of applications. For example, in heating, ventilation and air-conditioning (HVAC) applications, air may be heated, cooled, humidified, dehumidified, filtered or otherwise treated for delivery into residential, commercial or other spaces.

Needs exist for improved systems and methods of treating and delivering air for these and other applications. It is to the provision of improved systems and methods meeting these needs that the present invention is primarily directed.

BRIEF SUMMARY OF THE INVENTION

According to an embodiment of the present invention, an ion generator device includes a base, a sidewall projecting from the base to collectively form an interior storage compartment and to define an upper edge, a top portion engaged to the upper edge, at least one high voltage wire extending from the device, and a power supply for providing a voltage to the high voltage wire for producing ions.

According to another embodiment of the present invention, an ion generator device includes a sidewall that is generally circular in shape.

According to yet another embodiment of the present invention, an ion generator device includes at least one magnet within the base of the device.

According to yet another embodiment of the present invention, an ion generator device includes a transformer housed within the interior storage compartment and is engaged to the power supply and the at least one high voltage wire.

According to yet another embodiment of the present invention, an ion generator device includes two high voltage wires extending from the device, wherein one of the high voltage wires produces negative ions and the second high voltage wire produces positive ions.

According to yet another embodiment of the present invention, an ion generator device includes at least one bore within the top portion, whereby the at least one high voltage wire extends therethrough.

According to yet another embodiment of the present invention, an ion generator device includes an upper retention flange disposed the sidewall and extending therefrom.

According to yet another embodiment of the present invention, an ion generator device includes an LED light disposed on the top portion.

According to yet another embodiment of the present invention, an ion generator device includes a base that extends to an outer edge, a generally circular sidewall projecting from the base to form an interior storage compartment and defining an upper edge. The sidewall has an inner and outer sidewall surface. A top portion is engaged to the upper edge, a first and a second high voltage wire extending from the device, and a power supply for providing a voltage to the high voltage wire for producing ions.

According to yet another embodiment of the present invention, an ion generator device includes a first brush engaged to the first high voltage wire and a second brush engaged to the second high voltage wire.

According to yet another embodiment of the present invention, an ion generator device includes a first brush engaged to the first high voltage wire and a second brush engaged to the second high voltage wire, wherein the first brush and second brush contain bristles composed of a thermoplastic impregnated with carbon.

According to yet another embodiment of the present invention, an ion generator device includes an interior cavity that includes an epoxy.

According to yet another embodiment of the present invention, an ion generator device includes a first bore and a second bore within the top portion, whereby the first high voltage wire extends through the first bore and the second high voltage wire extends through the second bore According to yet another embodiment of the present invention, an ion generator device includes a lower retention flange with a hollow bore disposed therein, the lower retention flange is engaged to the device.

According to yet another embodiment of the present invention, an ion generator device includes a circuit board including a transformer disposed within the interior storage compartment.

According to yet another embodiment of the present invention, a method of producing ions includes providing an ion generator device including a base, a generally circular sidewall projecting from the base to form an interior storage compartment and to define an upper edge, a top portion engaged to the upper edge, at least one high voltage wire extending from the device, a power supply for providing a voltage to the high voltage wire for producing ions; and placing the ion generator device within the housing of the air handler unit.

According to an embodiment of the present invention, an ion generator device includes a generally circular base, a sidewall projecting from the base to collectively form an interior storage compartment and to define an upper edge, a top portion engaged to the upper edge, at least one high voltage wire extending from the device, and a power supply for providing a voltage to the high voltage wire for producing ions.

According to yet another embodiment of the present invention, an ion generator device includes a base that extends to an outer edge having a bottom side, a top side, an upper portion, and a bottom portion, wherein the upper portion is generally arcuate in shape, a sidewall projecting from the base, forming an interior storage compartment and defining an upper edge. The sidewall has an inner and outer sidewall surface. A top portion is engaged to the upper edge, a first and a second high voltage wire extending from the device, and a power supply for providing a voltage to the high voltage wire for producing ions.

BRIEF DESCRIPTION OF THE DRAWINGS

The present invention is illustrated and described herein with reference to the various drawings, in which like reference numbers denote like method steps and/or system components, respectively, and in which.

DETAILED DESCRIPTION OF THE INVENTION

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
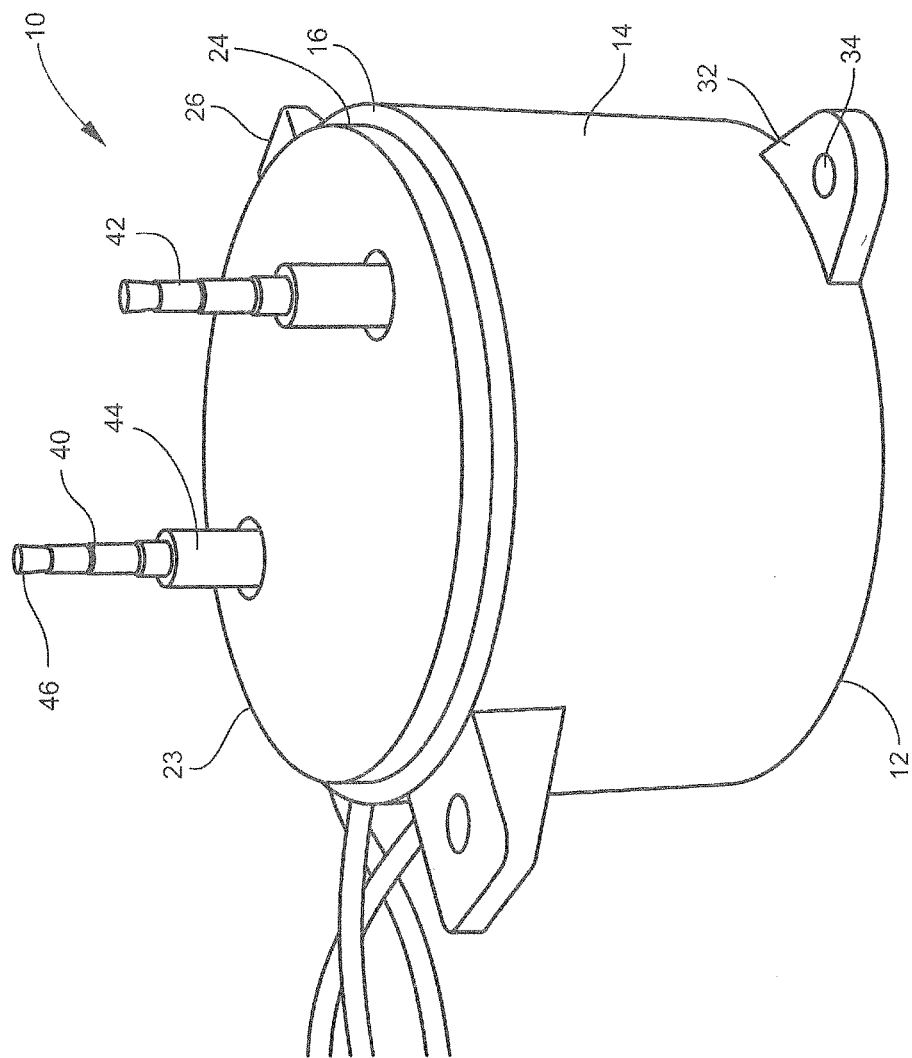
FIG. 1 is a perspective view of the device.
Figure 2:
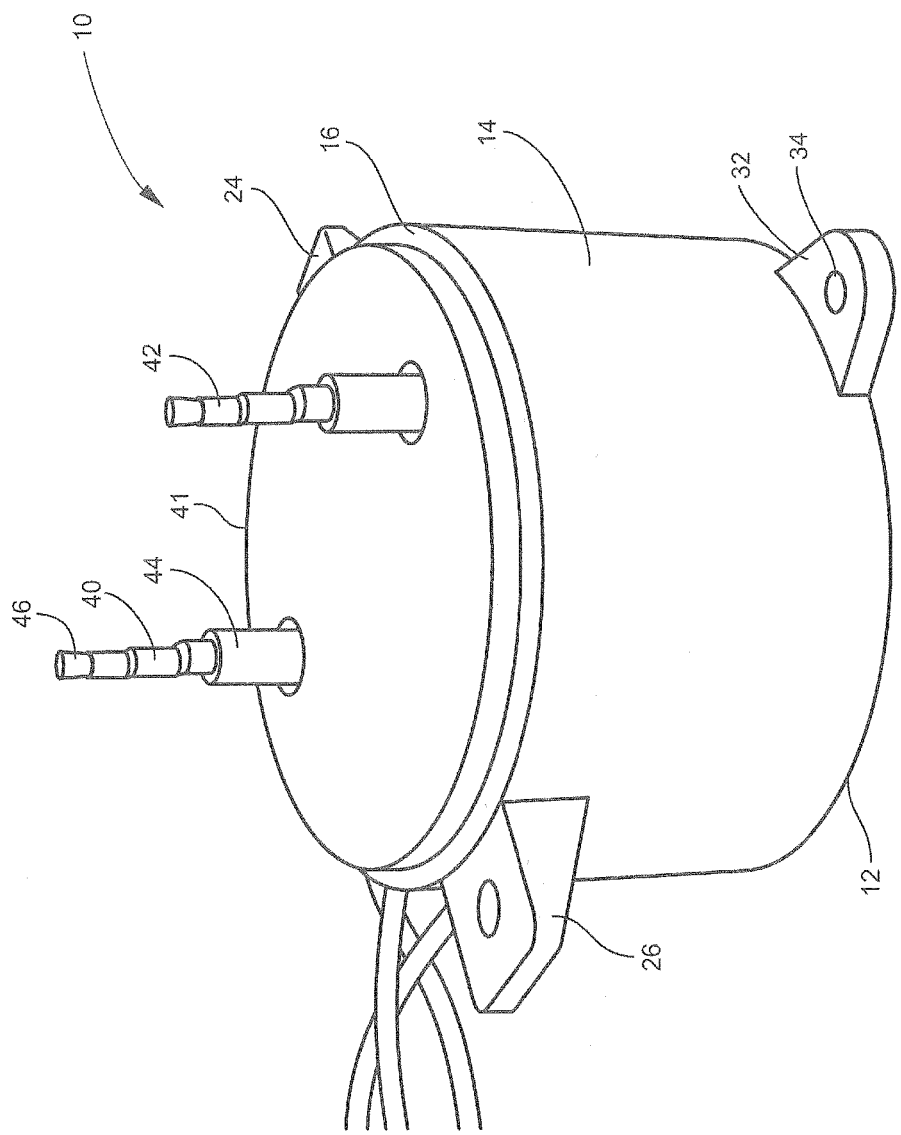
FIG. 2 is another perspective view of the device.

Referring now specifically to the drawings, and as illustrated in FIGS. 1 and 2, the ionization device is shown generally at reference numeral 10 that because of its shape allows air to easily flow over and around. The device 10 includes a base 12 that extends to an outer edge. A sidewall 14 extends from the outer edge of the base 12 to an upper edge 16. The sidewall 14 has an inner and outer sidewall surface 18, 20, respectively, forming an interior storage compartment. A top portion 24 is engaged to the upper edge 16 and enclosing the interior storage compartment.

The base 12 is generally circular in shape and has a bottom side and a top side. The sidewall 14 extending upwardly generally conforms to the shape of the base and is generally cylindrically shaped. The upper edge 16 of the sidewall 14 surrounds the generally cylindrically shaped sidewall 14 having a generally circular shape. The top portion 24 that is engaged to the upper edge 16 is also generally circular in shape.

The base 12 may be integral with the sidewall 14. Alternatively, the base 12 and sidewall 14 may be separate, wherein a first end of the sidewall 14 is disposed adjacent the outer edge of the base 12, and the second end of the sidewall 14 is disposed adjacent the top portion 24. The base 12 and sidewall 14 may be engaged to each other by an attachment device, such as an adhesive, screw, bolt, or the like. Likewise, the top portion 24 may be integral to the second end of sidewall 14. Alternatively, the top portion 24 and sidewall 14 may be engaged to each other by an attachment device, such as an adhesive, screw, bolt, or the like.

At least one upper retention flange 26 extends from the sidewall 14. The upper retention flange 26 extends outwardly from the sidewall 14 and generally planar to the upper edge 16. The upper retention flange 26 contains an upper portion, a bottom portion, and two side portions. A brace member 28 extends downwardly from each side portion of the upper retention flange 26. The brace member 28 provides stability and support to the upper retention flange 26 to withstand the stresses exerted upon the upper retention flange 26 when used to secure the device 10 to a wall, duct, or the like. The upper retention flange 26 also contains a bore that extends from the upper portion to the lower portion for allowing a retention device, such as a screw, bolt, or the like, to be inserted therethrough and selectively securing or engaging the upper retention flange 26 to a wall, duct, or the like.

As illustrated in FIGS. 1 and 2, the device 10 may have two upper retention flanges 26 that are in a spaced-apart relationship. As shown, the upper retention flanges 26 are disposed on opposed sides of the sidewall 14 for selectively securing or engaging the device 10 to a wall, duct, or the like. The upper retention flanges 26 engage the duct, and allow the device 10 to be mounted to the duct. Alternatively, the upper retention flanges 26 may be disposed on a side of the top portion 24.

Figure 3:
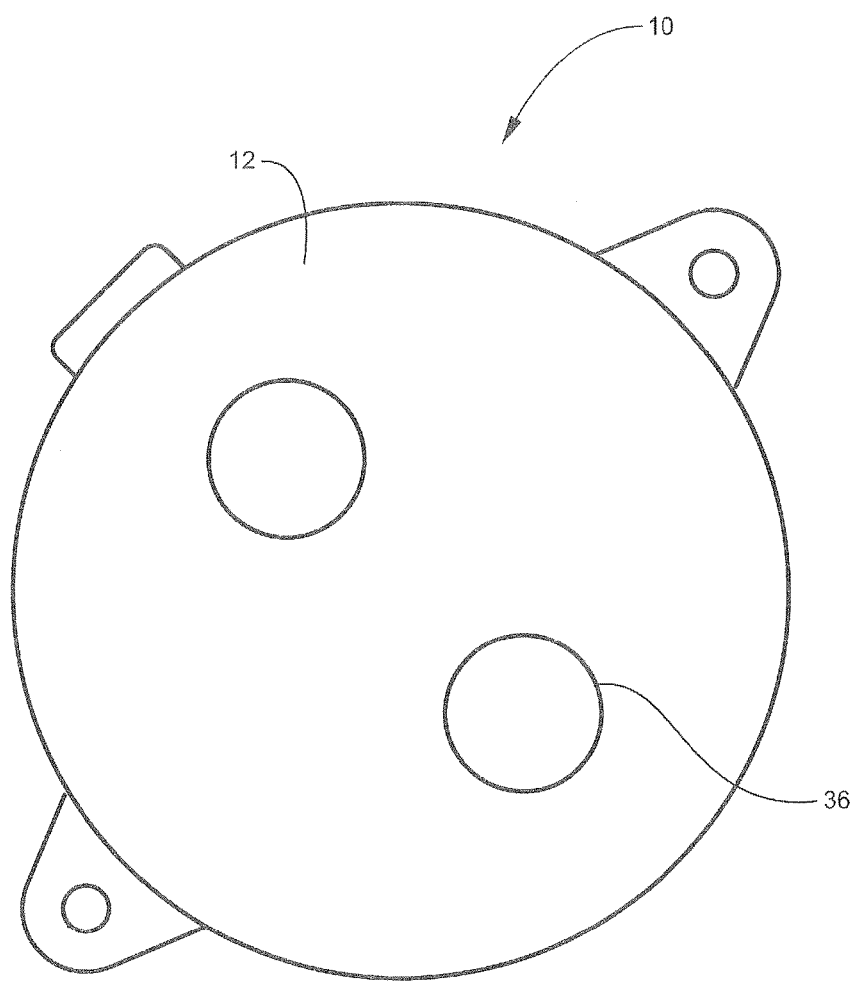
FIG. 3 is a bottom view of the device.

As shown in FIGS. 1, 2, and 3, the device 10 may also contain at least one bottom retention flange 32. The bottom retention flange 32 extends outward from the device 10. The generally triangular shape of the bottom retention flange 32 allows the bottom retention flange 32 to selectively secure or engage the device 10 to a confined space within a wall, duct, or the like. The bottom retention flange 32 provides stability and support for the device 10. The bottom retention flange 32 has an upper portion, a bottom portion, and two side portions. A bore 34 extends from the upper portion to the bottom portion of the bottom retention flange 32 for allowing a retention device, such as a screw, bolt, or the like, to be inserted therethrough and selectively securing or engaging the bottom retention flange 32 to a wall, duct, or the like. The bottom retention flange 32 is engaged to the exterior side of a duct, allowing at least the top portion 24 and a portion of the sidewall 14 to be inserted into the duct and flow of air.

As illustrated, the device 10 may have two bottom retention flanges 32 that are in a spaced-apart relationship. The bottom retention flanges 32 may be disposed on opposed sides of the sidewall 14 for selectively securing or engaging the device 10 to a wall, duct, or the like. Alternatively, the bottom retention flange 32 may be engaged to the side of the exterior of the base 12. The upper retention flange 26 and bottom retention flange 32 are offset from each other. In other words, the placement of the upper retention flange 26 is not "over top" or above the bottom retention flange 32. As illustrated, the upper retention flanges 26 are offset by 45 degrees from the bottom retention flanges 32.

The base 12 of the device 10 may also contain at least one magnet 36. The at least one magnet 36 may be generally circular in shape, and the exterior side of the base 12 of the device 10 contains a correspondingly shaped bore disposed on the bottom side for receiving the at least one magnet 36. As illustrated, the base 12 contains two bores for receiving one magnet 36 in each bore. The at least one magnet 36 may be recessed within the bore and flush with the bottom side of the base 12. As illustrated in FIG. 3, the device 10 contains two magnets 36 on the bottom of the base 12. The magnets 36 are designed to selectively secure the device 10 to a wall, duct, or the like.

The top portion 30 of the device 10 contains at least one opening 38 that extends therethrough to the interior storage compartment 22. A high voltage wire 40 extends through the opening 38. As shown in FIGS. 1 and 2, the device 10 contains two openings 38 and a first high voltage wire 40 extends through one opening and a second high voltage wire 42 extends through the second opening 38. In one embodiment, a hollow column 44 encircles the opening 38 and extends perpendicularly upward from the top portion 24 of the device 10 for providing support to the high voltage wires (40,42). As illustrated, a hollow column 44 encircles the opening 38 containing the first high voltage wire 40, and a hollow column 44 encircles the opening 38 containing the second high voltage wire 42. The end of the first and second high voltage wire (40,42) contains a brush 46 that contains a plurality of bristles that extend outwardly away from the brush 46. The brush 46 and its bristles may be made of any material that conducts electricity. In one embodiment, the bristles of the brush 46 are composed of a thermoplastic polymer imbedded with conductive material that allows the polymer to conduct electricity. For example, the bristles of the brush 46 may be composed of polypropylene or polyethylene and impregnated with carbon. Generally, the bristles of the brush 46 may contain between about 20 to about 80 wt % polypropylene copolymer or polyethylene copolymer, between about 5 to about 40 wt % talc, and from about 5 to 40 wt % carbon black. However, any other resistive, inductive, reactive or conductive plastic or non-metallic material may be utilized for the bristles of the brush 46.

The brush 46 is engaged to the end of the high voltage wires 40,42. In one embodiment, the brush 46 is crimped to the end of the high voltage wires 40, 42 extending outwardly from the device 10. In another embodiment, the brush 46 is engaged to the end of the high voltage wires 40, 42 extending outwardly from the device 10 by heat shrink. The high voltage wires 40, 42 come off the transformer 38 at 6500 volts, wherein the first high voltage wire 40 and associated brush 46 deposits a stream of negative ions into the surrounding air and the second high voltage wire 42 and associated brush 46 deposits positive ions into the surrounding air.

The device 10 preferably produces approximately equal amounts of positive and negative ions, regardless of airflow velocity or other conditions such as humidity or temperature. In example forms, the device 10 produces positive ions and negative ions in a concentration of at least about $10^9$ ions/second, and operates on 24VAC, 110VAC or 200VAC to 240VAC without the use of an external transformer. In alternate embodiments, the device generates negative ions only, or positive ions only, or generate negative ions and positive ions in unequal quantities. The device 10 optionally utilizes nano-electronic components allowing the device to be very compact, requiring less than 1 watt/ion generator module, for example less than 0.5 watts/ion module, and in further examples less than 0.36 watts per ion module.

In one embodiment, the top portion 24 of the device 10 may contain an LED bore that extends through the top portion 24 and into the interior storage compartment 22. A light emitting diode (LED) 41 is positioned over the LED bore and engaged to an LED wire that extends from a circuit board to the LED light. When current is flowing through the high voltage wires 40, 42, current also flows through the LED wire and illuminates the LED light, indicating the device 10 is operating. The top portion 24 contains a first power supply bore and a second power supply bore for receiving the positive and negative power supply wires that serve as the power supply source.

Figure 4:
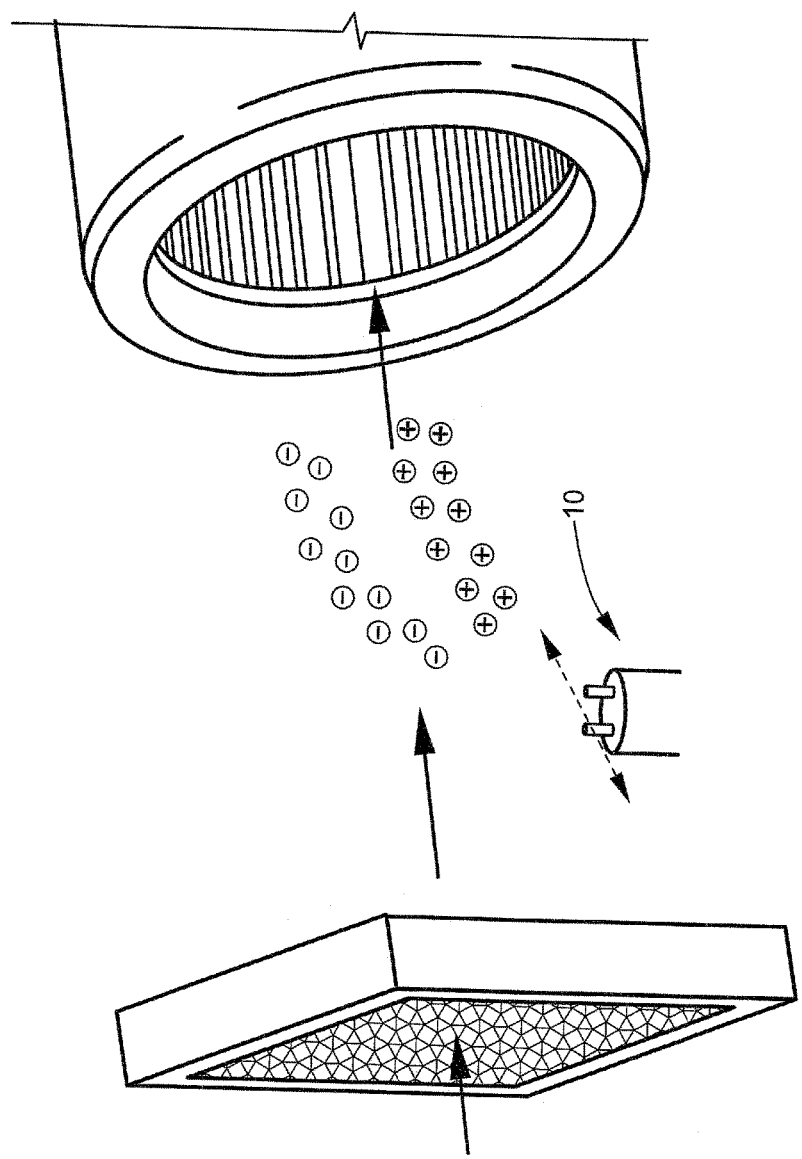
FIG. 4 is an exemplary view of the device in use.

FIG. 4 shows internal components of an individual air handler unit according to one embodiment of the invention. An inlet airflow flowing through a conduit such as the housing of the air handler unit or a duct is filtered through a filter such as a mesh, screen, paper, cloth or other filter media. A filtered airflow downstream of the filter is treated by discharge of bipolar ionization from the device 10 to form an ionized airflow. The bipolar ionization comprises a stream of negatively charged (−) ions, and a stream of positively charged (+) ions. The ionized airflow enters the inlet of a fan or blower for delivery to the treated air space, and is optionally heated or cooled by passing across or through a cooling coil or heating element. The coil, filter, device 10 and fan are optionally mounted within a housing of the air handler unit. Example modes of attachment of the device 10 include, without limitation, adhesive, hook-and-loop fasteners, straps, screws, clips or other mechanical fasteners, magnetic mounting, and/or mounting brackets or carriers affixed to or through the housing or associated ductwork. The mode of attachment may be inserted through a bore in the retention flange for engaging the device 10 to the housing of an air handler unit.

In one embodiment and use, the bipolar ion generator device 10 is positioned and secured in place within the housing of the air handler unit such that the electrodes $40^+$ and $40^-$ are aligned generally perpendicularly to the direction of the airflow across the ion generator device 10, to prevent recombination of the positively charged ions with the negatively charged ions. In other words, a vector representing the average flow velocity of the airflow is at approximately a right angle (90°) to an axis A extending between the electrodes $40^+$ and $40^-$. One or more ion generator device(s) 10 can be installed within the housing of each air handler unit, as required to generate the desired level of ion delivery for a given airflow, as may be determined by the airflow rate (CFM) of the fan and ion discharge rate of each ion generator device 10. The ion generator device(s) 10 are preferably positioned generally centrally in relation to the airflow or evenly distributed across the airflow path. If more than one ion generator is provided in an air handler unit, they are sufficiently spaced and positioned relative to one another to minimize recombination of positive ions with negative ions.

The treatment of air by delivery of bipolar ionization to an airflow within a conduit according to the systems and methods of the present invention may be utilized for various purposes. For example, application of bipolar ionization to an airflow within an HVAC conduit such as an air handler housing or duct may be utilized to abate allergens, pathogens, odors, gases, volatile organic compounds, bacteria, virus, mold, dander, fungus, dust mites, animal and smoke odors, and/or static electricity in a treated air space to which the airflow is directed. Ionization of air in living and working spaces may reduce building related illness and improve indoor air quality; and additionally can reduce the quantity of outside air needed to be mixed with the treated indoor air, reducing heating and cooling costs by enabling a greater degree of air recirculation.

The base 12, sidewall 14, top portion 24, at least one upper retention flange 26, and bottom retention flange 32 may be composed of a plastic. Alternatively, the top portion 24 may be composed of a plastic or foamed plastic material.

The base 12, sidewall 14, and top portion 24 are generally cylindrical in shape for allowing laminar air flow.

Figure 5:
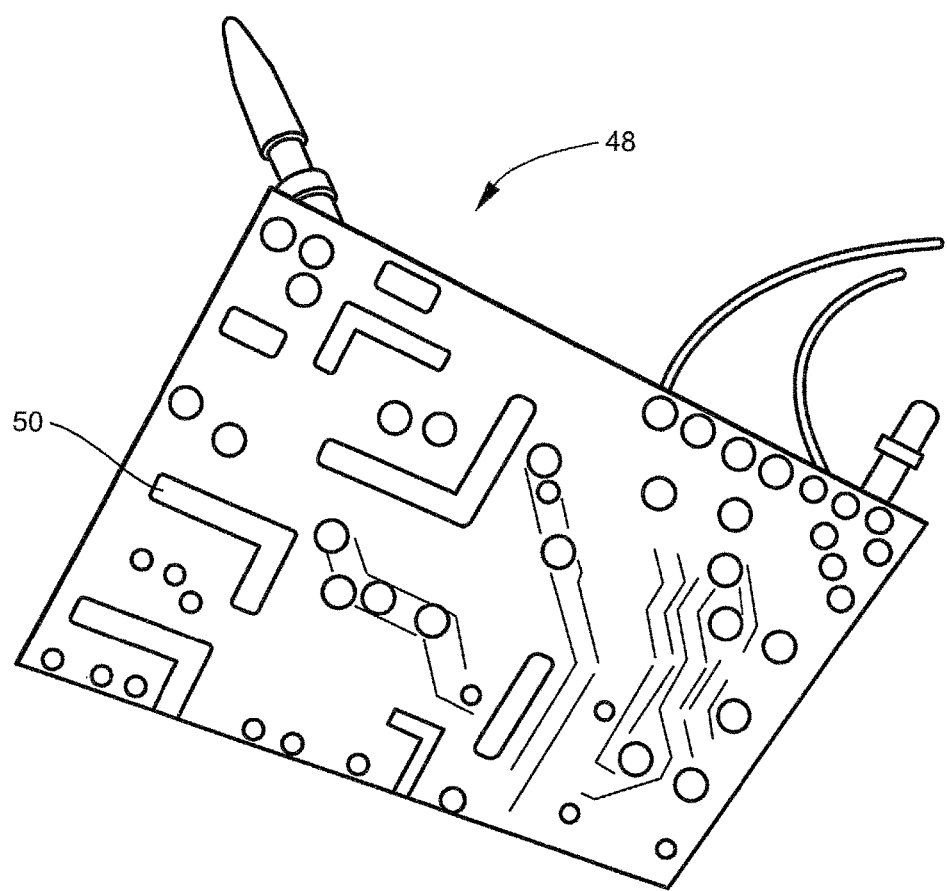
FIG. 5 is an exemplary circuit board.

An exemplary circuit board 48, as illustrated in FIG. 5, is contained within the interior storage compartment 22. The circuit board 48 is not continuous and has air gaps 50 contained therein. The purpose of the air gaps 50 is to prevent the high voltage from jumping to the low voltage area, and preventing the low voltage from jumping to the high voltage area. The interior storage compartment 22 may be filled with an epoxy. The circuit board 48 includes a power supply source, a transformer, and a first high voltage wire 40, and a second high voltage wire 42.

The top portion 24 may be covered by foam, or alternatively, the top side of the top portion 24 may be covered by a closed cell foam gasket 23 that acts as an air seal when mounted to a duct or the like. An LED 41 may also be disposed on the top portion 24 of the device 10.

Figure 6:
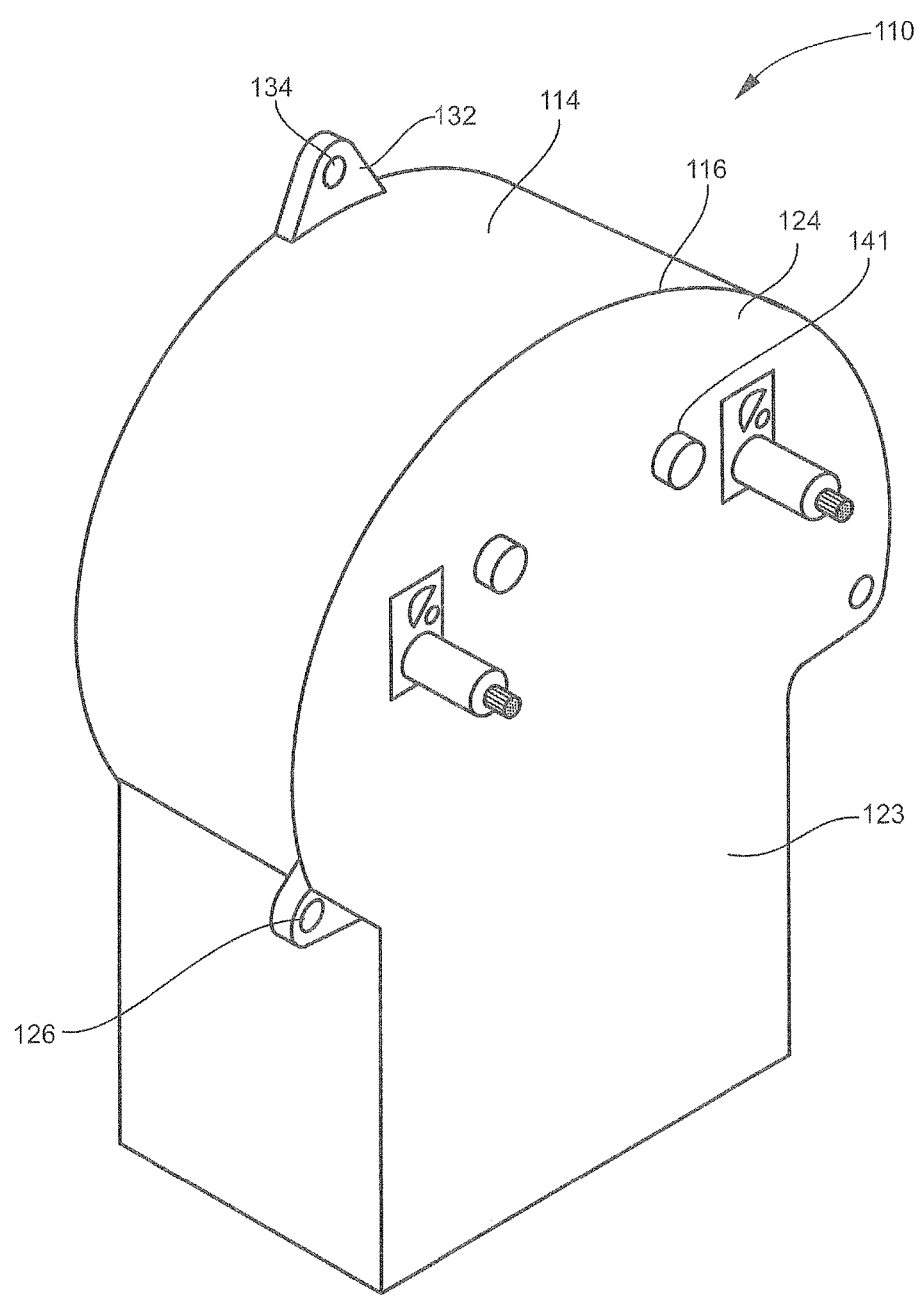
FIG. 6 is a front perspective view of an alternative embodiment of the device.
Figure 7:
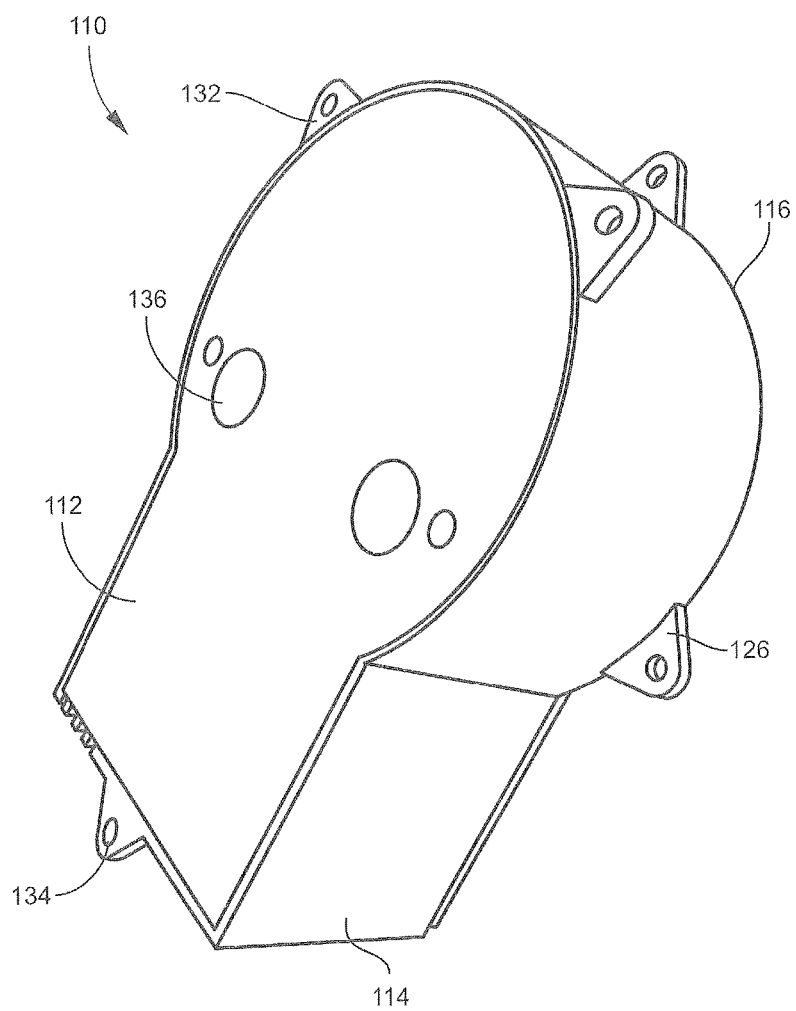
FIG. 7 is a back perspective view of an alternative embodiment of the device.

In an alternative embodiment and as illustrated in FIGS. 6 and 7, the ionization device is shown generally at reference numeral 110. The device 110 includes a base 112 that extends to an outer edge. A sidewall 114 extends from the outer edge of the base 112 to an upper edge 116. The sidewall 114 has an inner and outer sidewall surface, respectively, forming an interior storage compartment. A top portion 124 is engaged to the upper edge 116 and enclosing the interior storage compartment.

The base 112 has an arcuate upper portion and a generally square or generally rectangular bottom portion and has a bottom side and a top side. In other words, the base 112 has a generally keyhole shape. The sidewall 114 extending upward generally conforms to the shape of the base and has an arcuate upper portion and a generally square or generally rectangular bottom portion. The upper edge 116 of the sidewall 114 surrounds the generally cylindrically shaped sidewall 114. The top portion 124 that is engaged to the upper edge 116 has an arcuate upper portion and a generally square or generally rectangular bottom portion.

The base 112 may be integral with the sidewall 114. Alternatively, the base 112 and sidewall 114 may be separate, wherein a first end of the sidewall 114 is disposed adjacent the outer edge of the base 112, and the second end of the sidewall 114 is disposed adjacent the top portion 124. The base 112 and sidewall 114 may be engaged to each other by an attachment device, such as an adhesive, screw, bolt, or the like. Likewise, the top portion 124 may be integral to the second end of sidewall 114. Alternatively, the top portion 124 and sidewall 114 may be engaged to each other by an attachment device, such as an adhesive, screw, bolt, or the like.

At least one upper retention flange 126 extends from the sidewall 114. The upper retention flange 126 extends outwardly from the sidewall 114 and generally planar to the upper edge 116. The upper retention flange 126 contains an upper portion, a bottom portion, and two side portions. The upper retention flange 126 also contains a bore that extends from the upper portion to the lower portion for allowing a retention device, such as a screw, bolt, or the like, to be inserted therethrough and selectively securing or engaging the upper retention flange 126 to a wall, duct, or the like.

As illustrated, the device 110 may have two upper retention flanges 126 that are in a spaced-apart relationship. As shown, the upper retention flanges 126 are disposed on opposed sides of the sidewall 114 for selectively securing or engaging the device 110 to a wall, duct, or the like. The upper retention flanges 126 engage the duct, and allow the device 110 to be mounted to the duct.

The device 110 may also contain at least one bottom retention flange 132. The bottom retention flange 132 extends outward from the outer edge of the base 112. The generally triangular shape of the bottom retention flange 132 allows the bottom retention flange 132 to selectively secure or engage the device 110 to a confined space within a wall, duct, or the like. The bottom retention flange 132 provides stability and support for the device 110. The bottom retention flange 132 has an upper portion, a bottom portion, and two side portions. A bore 134 extends from the upper portion to the bottom portion of the bottom retention flange 132 for allowing a retention device, such as a screw, bolt, or the like, to be inserted therethrough and selectively securing or engaging the bottom retention flange 132 to a wall, duct, or the like. The bottom retention flange 132 is engaged to the exterior side of a duct, allowing at least the top portion 124 and a portion of the sidewall 114 to be inserted into the duct and flow of air.

As illustrated, the device 110 may have two bottom retention flanges 132 that are in a spaced-apart relationship. As shown, the bottom retention flanges 132 are disposed on opposed sides of the sidewall 114 for selectively securing or engaging the device 110 to a wall, duct, or the like. The upper retention flange 126 and bottom retention flange 132 are offset from each other. In other words, the placement of the upper retention flange 126 is not "over top" or above the bottom retention flange 132. As illustrated, the upper retention flanges 126 are offset by 45 degrees from the bottom retention flanges 132.

The base 112 of the device 110 may also contain at least one magnet 136 on the bottom side. The at least one magnet 136 may be generally circular in shape, and the base 112 of the device 110 contains a correspondingly shaped bore disposed on the bottom side for receiving the at least one magnet 136. As illustrated, the base 112 contains two bores for receiving one magnet 136 in each bore. The at least one magnet 136 may be recessed within the bore and flush with the bottom side of the base 112. The device 110 may contain two magnets 136 on the bottom of the base 112. The magnets 136 are designed to selectively secure the device 110 to a wall, duct, or the like.

The top portion 124 may be covered by foam, or alternatively, the top side of the top portion 124 may be covered by a closed cell foam gasket 123 that acts as an air seal when mounted to a duct or the like. An LED 141 may also be disposed on the top portion 124 of the device 110.

Figure 8:
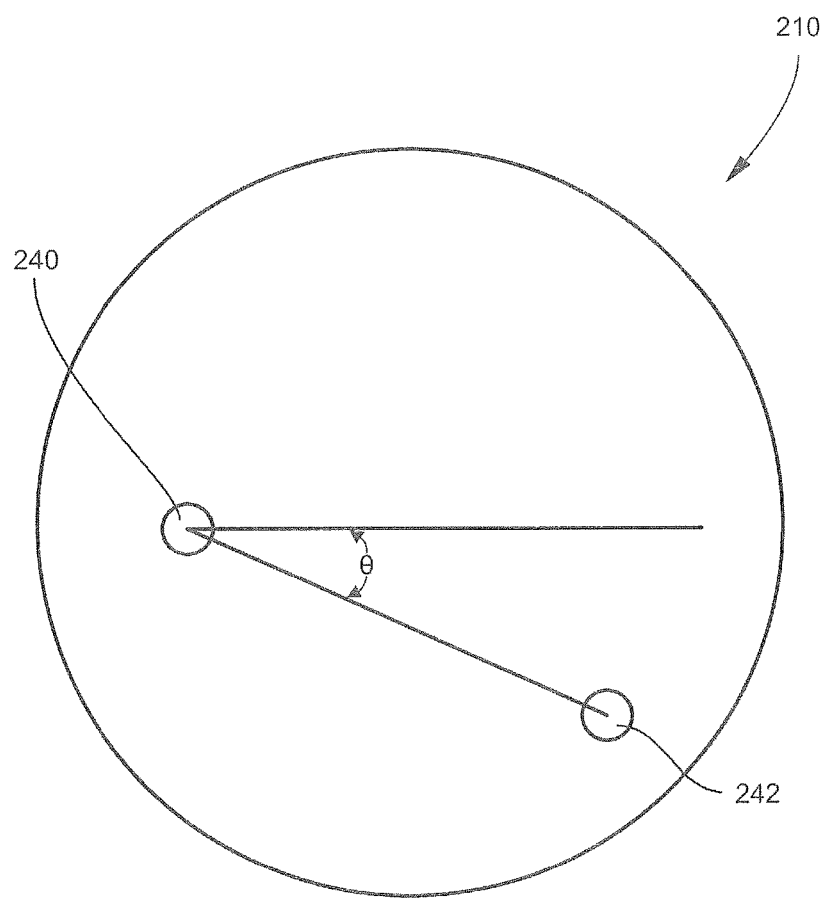
FIG. 8 is a top view of another alternative embodiment showing off set high voltage wires

As illustrated in FIG. 8, the high voltage wires 240, 242 may be offset from one another. In other words, instead of the high voltage wires 240, 242 being across from each other, the high voltage wires 240, 242 are offset or set apart by a predetermined degree. Preferably, the predetermined degree θ is preferably between about 1° to about 89° and more preferably between about 10° and about 70°. As illustrated, the first high voltage wire 240 is offset or set apart from the second high voltage wire by an angle θ that is between about 1° to about 89° and more preferably between about 10° and about 70°.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention and are intended to be covered by the following claims.

What is claimed is:

1. An ion generator device, comprising:
a generally circular base,
a sidewall having a first end and a second end, the first end adjacent to the base, forming an interior storage compartment and to define an upper edge; a top portion engaged to the upper edge;
a first high voltage wire and a second high voltage wire extending from the device, wherein the first high voltage wire is setoff from the second high voltage wire by an angle between about 10° and about 70°; a power supply for providing a voltage to the high voltage wire for producing ions.

2. The ion generator device of claim 1, wherein the sidewall is generally circular in shape.

3. The ion generator device of claim 1, wherein the first high voltage wire produces negative ions and the second high voltage wire produces positive ions.

4. The ion generator device of claim 1, further comprising a first bore and a second bore within the top portion, whereby the first high voltage wire extends through the first bore and the second high voltage wire extends through the second bore.

5. The ion generator device of claim 1, further comprising an upper retention flange disposed on the sidewall and extending therefrom.

6. The ion generator device of claim 1, further comprising an LED light disposed on the top portion.

7. The ion generator device of claim 1, further comprising at least one bore disposed within the bottom side of the base with at least one magnet disposed within the bore.

8. An ion generator device, comprising:
a base that extends to an outer edge having a bottom side, a top side, an upper portion, and a bottom portion, wherein the upper portion is generally arcuate in shape;
a sidewall projecting from the base, forming an interior storage compartment and defining an upper edge, the sidewall has an inner and outer sidewall surface; a top portion engaged to the upper edge;
a first high voltage wire and a second high voltage wire extend from the device, wherein the first high voltage wire is set apart from the second high voltage wire by an angle between about 1° and about 89°;
a power supply for providing a voltage to the high voltage wire for producing ions; and
at least one bore disposed within the bottom side of the base with at least one magnet disposed within the bore.

9. The ion generator of claim 8, further comprising a first brush engaged to the first high voltage wire and a second brush engaged to the second high voltage wire.

10. The ion generator of claim 8, further comprising a first brush engaged to the first high voltage wire and a second brush engaged to the second high voltage wire, wherein the first brush and second brush contain bristles composed of a thermoplastic impregnated with carbon.

11. The ion generator of claim 8, wherein the interior cavity includes an epoxy.

12. The ion generator of claim 8, wherein one of the high voltage wires produces negative ions and the second high voltage wire produces positive ions.

13. The ion generator device of claim 8, further comprising a first bore and a second bore within the top portion, whereby first high voltage wire extends through the first bore and the second high voltage wire extends through the second bore.

14. The ion generator device of claim 8, further comprising a bottom retention flange with a hollow bore disposed therein, the retention flange is engaged to the device.

15. The ion generator device of claim 8, further comprising an LED light disposed on the top portion of the device.

16. A method of producing ions, comprising:
providing an ion generator device including a base, a generally circular sidewall projecting from the base forming an interior storage compartment and defining an upper edge, a top portion engaged to the upper edge, a first high voltage wire and a second high voltage wire extending from the device, wherein the first high voltage wire is setoff from the second high voltage wire by an angle between about 1° and about 89°, a power supply for providing a voltage to the high voltage wire for producing ions; and placing the ion generator device within the housing of the air handler unit.

17. The method of producing ions according to claim 16, wherein the first high voltage wire produces negative ions and the second high voltage wire produces positive ions.

18. The method of producing ions according to claim 16, further comprising an ion generation device including a brush with bristles composed of a thermoplastic impregnated with a carbon engaged to the at least on high voltage wire.

19. The method of producing ions according to claim 16, further comprising an ion generation device including an upper retention flange with a hollow bore disposed therein, the retention flange is engaged to the device.

* * * * *